United States Patent [19]
Boucher

[11] Patent Number: 6,039,921
[45] Date of Patent: Mar. 21, 2000

[54] LIQUID PHASE DISINFECTION/ STERILIZATION WITH MICROWAVE ENERGY

[76] Inventor: Raymond M. G. Boucher, 5602 N. Scottsdale Rd., Scottsdale, Ariz. 85253

[21] Appl. No.: 08/978,396

[22] Filed: Nov. 25, 1997

[51] Int. Cl.$^7$ .................. A61L 2/12; A61L 2/16
[52] U.S. Cl. .................. 422/21; 422/28; 424/405; 424/616
[58] Field of Search ............ 422/21, 28; 424/405, 424/616; 514/557

[56] References Cited

U.S. PATENT DOCUMENTS

| | | |
|---|---|---|
| 3,753,651 | 8/1973 | Boucher . |
| 3,948,601 | 4/1976 | Fraser et al. . |
| 4,207,286 | 6/1980 | Boucher . |
| 4,321,232 | 3/1982 | Bithell . |
| 4,643,876 | 2/1987 | Jacobs et al. . |
| 5,004,757 | 4/1991 | Boucher .................. 514/694 |
| 5,077,008 | 12/1991 | Kralovic et al. .................. 422/37 |
| 5,344,652 | 9/1994 | Hall, II et al. . |
| 5,508,046 | 4/1996 | Cosentino et al. . |
| 5,759,486 | 6/1998 | Peterson .................. 422/21 |

OTHER PUBLICATIONS

Translation: Kuchma et al, "Combined Action of microwave radiation and hydrogen peroxide . . . *Pseudomonas Aeruginosa*," Zh. Mikrobiol., Epidemiol. Immunobiol., see entire document, 1990.

Translation: Kuchma et al, "Study of the mechanisms of combined action of SHF microwaves and hydrogen peroxide . . . microorganisms," Biofizika, see entire document, 1996.

Kuchma et al. "Combined action of microwave radiation and hydrogenperoxide on the viability and structure of *Pseudomonas aeruginosa*," Zh. Mikrobiol., Epidemiol. Immunobiol. (in Russian), vol. 9, pp. 20–23, 1990.

Kuchma et al. "Study of the mechanisms of combined action of SHF microwaves and hydrogen peroxide on viability of microorganisms," Biofizika (in Russian), vol. 41, No. 2, pp. 433–439, 1996.

T. Kuchma, Synergistic Effect of Microwave Heating and Hydrogen Peroxide on Inactivation of Microorganisms, 1998, pp. 77–87, *Journal of Microwave Power and Electromagnetic Energy*, vol. 33, No. 2.

T. Kuchma, Modification of Bactericidal Effects of Microwave Heating and Hyperthermia by Hydrogen Peroxide, 1997, pp. 205–214, *Journal of Microwave Power and Electromagnetic Energy*, vol. 32, No. 4.

Seymour S. Block, Peroxygen Compounds, pp. 167–168, *Disinfectants and Antiseptics*, Chap. 9.

Steriller gets FDA OK for expanded use, Sep. 1997, p. 10, *Infection Control & Sterilization Technology*.

*Science Watch*, news release of Jun. 20, 1989 in the *New York Times* (C.6). Microwave Sterilizer Developed.

*Primary Examiner*—Elizabeth McKane
*Attorney, Agent, or Firm*—Locke Liddell & Sapp, LLP

[57] ABSTRACT

Dental, medical and laboratory instruments may be disinfected and/or sterilized by exposure to a biocidal solution composed of hydrogen peroxide and a weak acid in the presence of microwave irradiation. The process typically occurs at low temperature, generally less than 65° C. In a preferred embodiment, the contaminated instruments are placed in a microwave transparent vessel containing the biocidal solution. A lid is placed over the vessel and the vessel is then placed into a cavity of a microwave oven and irradiated for a very short period of time. At the end of irradiation, instruments are safely and aseptically removed from the cooled container.

33 Claims, No Drawings

LIQUID PHASE DISINFECTION/ STERILIZATION WITH MICROWAVE ENERGY

BACKGROUND OF THE INVENTION

1. Field of the Invention

This invention relates to a process for fast high level disinfection/serialization of dental, medical or laboratory instruments in liquids through a synergistic combination of microwave irradiation with a sterilant/disinfectant containing hydrogen peroxide and weak organic acid.

2. Description of the Prior Art

In the past, several unsuccessful attempts have been made to decontaminate dental instruments within microwave ovens at a frequency of about 2450 MHZ. Metal instruments were quickly overheated. Further, intense microwave fields created localized arcing which pit metal surfaces. Although this could be somewhat minimized by proper humidification, instruments having different dielectric characteristics reach widely different temperatures even when irradiated with the same exposure time. Therefore, it is impractical to process metal tools in the presence of other instruments containing plastics or rubber type components.

In the early eighties, there was a revival of the use of microwave fields as a means to create gas plasma with biocidal characteristics. A gas plasma is a highly ionized body of gas which is created, for instance, in an enclosed chamber under vacuum using radio frequency (RF) or microwave energy. These types of plasma are classified as low energy plasma and are called non equilibrium or glow discharge gas plasmas. Vacuum pressure is also an important variable. The deeper the vacuum, the greater the energy and reactivity of the plasma.

U.S. Pat. No. 3,753,651 discloses an experimental set up to gas plasma sterilize instruments. This patent describes a chamber transparent to radiation which may be inserted into the microwave oven cavity. The chamber further contains both the sterilant gas (or vapor) and the instruments to be decontaminated. Other approaches are mentioned in U.S. Pat. No. 3,948,601 and U.S. Pat. No. 3,968,248 which describe continuous or batch sterilization within a highly reactive plasma atmosphere.

Industrial sterilization systems based upon the principles described in these patents have been successfully developed using hydrogen peroxide (STERRAD) or peracetic acid (PLAZLYTE) as the active vaporized agents in the gas plasma. Unfortunately these industrial processes are rather complicated because they require creation and maintenance of a uniform stable gas plasma through vacuum control while also accurately injecting various amounts of gas sterilants.

A small reliable and inexpensive dental instrument sterilizer cannot be based upon the sophisticated designs developed for gas plasma industrial or hospital systems. In the late 1980s, attempts to build dental sterilizers based upon gas plasma technology wherein traces of biocidal agents were injected into the gas phase, were reported. See, for instance, "Science Watch", June 20, 1989, New York Times. However no prototype or equipment ever reached the market despite promising news releases. One obvious reason was that to achieve sterilization according to FDA requirements (6 logs kill of spores) the best large size hospital plasma units required a contact time of 4 hours (PLAZLYTE with peracetic acid) or 90 minutes (STERRAD with hydrogen peroxide).

Another reason for the failure to develop a gas plasma sterilizer for dental instruments has been cost. Gas plasma sterilization is an expensive and delicate technology due to the difficult stabilization of plasma gases. Attempts to scale down such systems have failed. Inexpensive systems are needed which are capable of achieving sterilization or high level disinfection within a very short contact time with a minimum risk of corrosion for dental tools.

SUMMARY OF THE INVENTION

Disinfection and/or sterilization proceeds by liquid chemical sterilization with microwave energy versus gas plasma. Liquid chemical sterilization with microwaves does not deal with reactions in gas but instead in liquid phase irradiated by microwaves. The disinfection and/or sterilization of medical, dental or other scientific instruments in accordance with the invention may proceed by exposure of the instrument to a biocidal solution comprising hydrogen peroxide and a weak acid. The instruments are further exposed to the biocidal solution in the presence of microwave irradiation at a temperature less than or equal to 65° C.

The contaminated instruments are placed in a vessel containing the biocidal solution. The vessel may then be placed into a microwave oven and irradiated for a short period of time.

DETAILED DESCRIPTION OF THE PREFERRED EMBODIMENTS

The method of invention provides a quick and efficacious means of combining the action of microwave irradiation with two inexpensive chemical agents. As defined by the EPA as well as the FDA, high level disinfection consists of substantial destruction of bacterial endospores while achieving complete kill of the most resistant vegetative organisms, such as *Mycobacterium tuberculosis* var. *bovis*.

The method of the invention is of particular significance in dental and doctor offices which are typically small areas. In such offices, it is typically necessary for the disinfection/sterilization units to be capable of handling quick turnover of instruments. In addition, biocidal solutions employed in such areas need to be odorless.

In accordance with the invention, medical, dental or laboratory instruments, generally metallic in nature, are submerged in the biocidal solution. Alternatively, the biocidal solution may be added to the vessel containing the contaminated instrument. The vessel containing the biocidal solution and instrument(s) is then placed within a microwave energy source, such as a microwave oven. Thus, there is no "arcing" between the walls of the microwave energy source and the instruments. Arcing only occurs when metals are directly exposed to the microwave energy source.

The instrument may be one used in a hospital, veterinary establishment, dental office, or medical doctor's office, coroner's office and/or laboratory or other establishment which requires the use of sterilized or bacteria-free instruments.

The biocidal solution employed in the invention is composed of hydrogen peroxide and a weak organic acid. Suitable weak organic acids are those having a pKa greater than or equal to 4. Such acids include acetic acid, citric acid and lactic acid. Typically, the hydrogen peroxide employed in the invention is between 8 to about 11, most typically 10, weight percent. The peroxide solution is diluted down to about 6 or about 7.5 weight percent with an aqueous solution of the weak organic acid.

While the weak organic acids or their salts are not the active ingredients in the biocidal composition of the invention, they capture some oxygen from the hydrogen peroxide molecule. The captured oxygen enters into a —OOH group which is either very reactive per se or later releases a highly reactive oxygen atom. Thus, the improved biocidal efficacy observed in the biocidal composition of the invention is the result of synergistic biocidal mechanisms created by combining microwave energy, heat and oxidizing chemical reactions.

The composition of the invention may further contain a non ionic surfactant. Suitable non ionic surfactants are ethoxylates of isomeric linear alcohols such as TERGITOL from Union Carbide, TRITON from Rohm and Haas Co., PLURONIC from BASF Wyandotte Corporation and alkali metal alkylaryl sulfates and sulfonates.

The biocidal composition may further contain a stabilizer such as methylparaben or acetominophen. Generally less than 1 weight percent of stabilizer is employed.

In addition, the pH of the biocidal solution is between about 1 to about 7. Suitable buffering agents include alkali metal carbonates, bicarbonates, phosphoric acid, phosphates and borates, carboxylic acids, piperazine, sulfonic acid, organic carboxylate salts, and mixtures thereof. Preferred are monobasic potassium or sodium phosphate with anhydrous dibasic sodium phosphate, phosphoric acid, mono or disodium phosphate, maleic acid, trisodium citric acid, citrate-phosphate buffer, succinic acid, cacodylate buffer, n-(2-acetamido) iminodiacetic acid, piperazine-n, $n^1$-bis (2-ethane sulfonic acid), and 2 (n-morpholino) ethane sulfonic acid. Particularly preferred are monobasic potassium, sodium phosphate and anhydrous dibasic sodium phosphate and mixtures thereof.

Further, the composition may contain an anticorrosive agent such as benzotriazole, tolytriazole, sodium molybdate or benzoate.

In a preferred embodiment, the hydrogen peroxide solution is poured into the container containing the contaminated instruments. The weak organic acid is then added to the hydrogen peroxide solution. This biocidal solution renders unnecessary the use of low concentration glutaraldehyde solutions which often display satisfactory sporicidal activity under microwave excitation but release toxic glutaraldehyde vapor at the end of the processing period once the lid of the vessel is opened and the instruments are removed. Contrary to glutaraldehyde based sterilizing solutions, hydrogen peroxide formulations provide fast cidal action without the release of toxic vapors at the end of processing (when removing the disinfected instruments from the irradiated solutions).

With microwave irradiation, the biocidal composition of the invention releases only small amounts of non toxic organic acid, hydrogen peroxide, water and oxygen - none of which are dangerous from the environmental view point.

The container for use in the invention may be any container which is safe and transparent to microwave energy including those containers of appropriate shape made of glass ceramic (CORNINGWARE tin, PYROCERAM, etc), heat resistant glass (PYREX), microwave safe plastics (typically those used for an autoclave) as well as pottery, stoneware, porcelain or even paper. Preferred are FLASH-PAK® and the Rubbermaid SERVIN SAVER plastic container since if the container is overheated the lid rim is designed to quickly release excess steam due to sudden increases in vapor pressure. (This is not an issue if disinfection is conducted at an end temperature of the biocidal composition lower than 65° C.)

In a preferred embodiment, the instruments to be disinfected/sterilized may be placed on a tray which is, in turn, inserted into the vessel. The tray most desirably has openings—such as horizontal slits of approximately 2 to 5 mm in diameter—to increase the flow of biocidal solution to the contaminated instruments. Alternatively, the tray may be meshed having openings of about 2 to about 5 mm.

The method of the invention further provides an ultrafast means of disinfection unlike conventional means of heating (conduction, convection, etc.) which create a lot of drawbacks from the corrosion view point.

The contaminated instrument(s) is exposed to microwave irradiation and the biocidal composition for a time and at a temperature sufficient to disinfect or sterilize the instrument depending upon the objective of the one performing the operation.

Conventional heat does not have the same effect as microwave heat on microorganisms and their surroundings on account of fundamental differences between conventional thermal energy and microwave energy. Microwave energy is coherent electromagnetic energy. In other words, it is ordered. As such, its characteristics may readily be identified and controlled with precision. Thermal energy, on the other hand, has random disordered characteristics which are not so easily controlled.

Although the term microwave, in general, may cover a rather wide range of frequencies (from 100 MHZ up to several hundred thousand MHZ), in a preferred embodiment of the invention the frequency is between about 100 to about 23,000 MHZ. Microwave oven outputs are typically rated according to the International Electrotechnical Commission (IEG) 705 test procedure in compliance with the standards set by the FCC. Most commercial ovens are rated with outputs between about 500 and about 900 watts at a frequency of 2450 MHZ. The minimum average power density should be at least 0.01 W/cm$^3$.

In an alternative embodiment, the microwave irradiation may be a continuous or pulsed wave emission having a repetition rate of the order of between about one per nanosecond to about one per minute.

The mechanism through which the microwave heating occurs at such frequencies is based upon the dipole moment or "polarization" of the molecules of the irradiated substance. When the polar molecules (absorbed water in cellular organisms for instance) are subjected to a strong alternating field, their rapid reorientations within the field create internal friction resulting in heat. Microwave transfer of energy takes place directly without the necessity of an intermediate medium such as a hot surface or a high temperature air stream. Energy transfer occurs wherever the field penetrates. No contact with the substance itself is required. Microwave heating eliminates the inherent inefficiency of transferring heat from an external source to the processed loan. Since microwave energy can be switched on to full power levels and off again by simply flipping a switch, the time lags associated with thermal processes is eliminated. This, indeed, is extremely important for instance to a dentist because it shows that he does not need to maintain a permanent heating system which continuously will create toxic vapors (case of glutaraldehyde) when introducing equipment or removing it from the sterilant container.

While thermal death of bacterial cells and spores is generally logarithmic, sigmoidal curves is not uncommon. The theory called "The Distribution of Resistance" points out the existence of non-uniform heat resistant spores. When applying heat to a microorganisms population (spores, for instance) deviation from the logarithmic nature of the survival curve is generally attributed to two basic factors: (1)

The presence of a hump or "lag" in the initial portion of the survival curve due to heat "activation;" and (2) the presence of a tailing of the final portion due to the presence of the more resistant variants in the population.

An energy of "activation" is generally necessary to initiate a chemical or biological process. In the case of spores, it is the energy necessary to release spores from their dormant state to begin their germination process. There is also an activation energy requirement to inactivate (lethal effect) microorganisms. Heat activation and inactivation both obey first order kinetics in combination and in that order. The moment a spore becomes activated it is subjected to the inactivation law. The effect of heat on microorganisms is the result of enzyme inactivation, proteins denaturation or both. This is, in other words, the integer of several complex phenomena. The type of heat flux (dry or moist), the manner into which the heat is generated or penetrates through the microorganisms (convection, conduction, radiation, etc) are, therefore, extremely important. This, indeed, could explain the faster killing rates observed with microwave energy which acts at once at molecular level and creates a coherent state of molecular turbulence throughout the entire irradiated mass.

Two other phenomena may also contribute to an explanation of the faster microwave cidal action on microorganisms present on the surface of contaminated instruments or in the liquid sterilant. The first phenomenon is the interaction of intense microwaves with the molecular structure of the liquid disinfectants. Several overlapping phenomena have been observed such as: high speed molecular oscillations which produce chemical bonds breaking, accelerated diffusion of ions through membranes, electrical charges modification at interfaces or even pH variations. The second phenomenon recognizes that microwaves may affect a metabolic system distinct from that of thermal energy.

Studies in soil sterilization indicated that a large soil fungus (*Rhizoctonia solani*) was killed at a temperature about 10° C. below that of its normal thermal death point. Another fungus (*Verticillium albo-atrum*) with extremely small spores was killed at about 3° C. below its lethal temperature. Non-spore forming bacteria are, in general, killed by microwave energy at points as much as 10° C. below thermal death point.

Regarding chemical bond cleavage, a few seconds irradiation at 2450 MHZ of 0.1 N solutions of NaOH produces hydrogen peroxide at a rate of about 0.01% every five seconds. The temperature at the end of three 10 second (i.e. 30 seconds) exposures is about 100° C. When similar samples are treated in a water bath to the same temperature, no hydrogen peroxide is detected with the UV absorption technique. This, among other things, demonstrates that the result of chemical bond breakage leads to the production of new chemicals or radicals with sporicidal or bactericidal characteristics.

Another important advantage of the present invention is the simplicity of the process which enables the dentist, doctor or technician to safely load contaminated instruments into the vessel. The vessel is typically transparent to microwave irradiation. The vessel is covered with a lid. The loaded vessel with its lid is then placed into a microwave oven cavity and it is irradiated during a few minutes. In a preferred embodiment, a switch is used to activate the irradiation for the time chosen by the experimenter for high level disinfection. Following the conclusion of irradiation, the vessel is cooled down a few minutes before the lid is open for safe aseptic removal of the instruments. Where a tray is used, the tray may be slightly shaken to rid it of the liquids which may have remained on the surfaces of the instruments prior to removal. The whole operation takes only a few minutes and there is no release of toxic vapors into the atmosphere. The biocidal solution in the vessel may be reused as long as the peroxide content is in excess of about 6 weight percent.

The process of the invention is further normally conducted at temperatures not to exceed 65° C., typically between about 54 to about 65° C. Such temperatures do not create problems with high vapor pressure in the irradiated vessel.

The invention has particular applicability in the dental field since 10% hydrogen peroxide is available at corner drugstores since it is typically used in hair bleaching, etc. The hydrogen peroxide may be poured into a container transparent to microwaves. A mark may then be made on the plastic to indicate a the upper level of the solution of peroxide to be poured into the container after positioning the instruments to be decontaminated. A second level mark may be made to indicate the amount of a weak acid, such as 5% commercial vinegar) to be added to the container. The lid is placed into the container and the container is then placed into the microwave. The microwave is operated at approximately 2450 MHZ.

The process of the invention proceeds at a faster rate than autoclaving. In the process of the invention, the container is radiated slightly more than 0.01 watt/cm$^3$ in the loaded cavity. Disinfection of the instruments occurs in about 3 to about 5 minutes at a temperature less than 65° C. No additional time is needed for the removal of sporicidal activity. This is in contrast to an average 20 minute contact time with steam sterilization in an autoclave and a ten hour contact time for liquid sterilants, for instance CIDEX. The loaded container may then be removed from the cavity, cooled and opened. Decontaminated residues, with toxic residuals removed, may then be aseptically removed.

In light of the predictability in the requisite time for decontaminating the instrument, the microwave energy source may be set on a timer, such as by the sound of an automatic acoustic signal on a microwave oven.

The invention may further be employed to sterilize medical and dental instruments. Sterilization can be achieved in about 8 to about 12 minutes, typically around 10 minutes. This is in sharp contrast to the 10 hours needed presently with glutaraldehyde containing solutions.

EXAMPLES

Example 1

A biocidal solution was prepared by adding a solution of hydrogen peroxide into a container. A weak organic acid, such as acetic acid, was then added to the container containing the hydrogen peroxide. The temperature in the liquid phase was permitted to increase until approximately 55 to about 60° C. The exposure time was determined by the volume of liquid being irradiated. Table 1, for instance, illustrates that 8 minutes of irradiation time is needed for a 2000 cc container, 3 minutes for a 750 cc container and a little less than one minute for a 250 cc container. Adding metal instruments into the irradiated solution slightly decreased the exposure time.

The operating parameters were as follows:

Microwave unit: Dualwave 2-Microsystem General Electric

Power Rating: 700 watts frequency 2450 MHZ Q25 MHZ)

Fresh tap water: Starting temperature 26.7° C.

Volume of irradiated liquid: 250 cc (1 quart vessel), 750 cc (2 quarts vessel) and 2000 cc (1 gallon vessel)

Results are illustrated in Table 1:

TABLE 1

| Irradiation | End-Temperature in 3 vessels containing: | | |
|---|---|---|---|
| in min. | 250 cc | 750 cc | 2000 cc |
| 0.5 | 42.2 (108° F.) | | |
| 1.0 | 58.9 (138° F.) | 35 (95° F.) | |
| 1.5 | 70.0 (15° F.) | | |
| 2.0 | 84.4 (184° F.) | 45 (13° F.) | |
| 2.5 | 95.0 (208° F.) | | |
| 3.0 | | 55.6 (132° F.) | |
| 4.0 | | 63.9 (147° F.) | |
| 5.0 | | 78.3 (173° F.) | 54.4 (130° F.) |
| 6.0 | | 85.0 (185° F.) | |
| 8.0 | | | 65.6 (150° F.) |
| 11 | | 77.2 (171° F.) | |
| 14 | | | 83.3 (182° F.) |

The biocidal composition of the invention fulfills high level disinfection in a few minutes (2 to 5 min) without the creation of noxious vapors in the atmosphere at the end of processing (when the lid is removed), Example 2

Tests were conducted with a General Electric Dualwave 2-microsystem whose cavity had the following dimensions: height: 11 inch, width: 16 inch, depth: 13½ inch. Magnetron was emitted at a nominal frequency of 2450 MHZ (±25 MHZ). The AC line voltage was single phase 120 V, 60 HZ. The AC power input to the Magnetron was 1186 Watts and the average power microwave output in the cavity (1.4 CF) was approximately 700 Watts.

Inside the cavity was placed a Rubbermaid microwave container (11" L, 6½" W and 2½" H) rated as a 2 quarts unit (1.9 liter) and having a capacity of 750 $cm^3$ for the biocidal composition.

Biocidal composition A was made of two active chemicals: a hydrogen peroxide solution (10%) which was poured first into a container and diluted with vinegar of 5 weight percent acidity. The final content in hydrogen peroxide was between 6 and 7.5 weight percent. The following dental tools were then submerged into the liquid: one plastic filling WI by Henry Schein, a 5 DE Explorer by HU-Friedy, one SE CS mirror handle by HU-Friedy and a front surface mirror from the same company. Between the instruments and inside the liquid disinfectant were placed ten SPORDEX bacterial spore strips from American Sterilizer. The *Bacillus subtilis* population of each strip averaged about 100,000. These strips are currently being used for checking ETO sterilization in gas phase but they have also been accepted by the FDA for liquid chemical sterilization monitoring. Since each package of SPORDEX contained several strips, half of them were used for the tests and the other half kept as a control.

The microwave surface sterilizer was turned on and kept running for about 3 minutes to reach an end temperature close to 60° C. The container lid was then opened. The dental tools and spore strips were removed under sterile conditions. The strips were individually placed in labeled test tubes, each containing 25 $cm^3$ of sterile fluid thioglycollate medium (FTM). The control strips left unsterilized were also placed into test tubes containing the same medium. *B. subtilis* was incubated at 37° C. for up to seven days. Cultures producing turbidity were recorded as positive for growth. Cultures not producing changes after seven days of incubation were recorded as negative for growth (ie, sterile). The results are reported in Table 2. (Operating parameters: 10 *B. subtilis* strips and 10 control strips used in each experiment. Microwave frequency: 2450 MHZ; energy density: 0.018 watt/$cm^3$.)

TABLE 2

| Experimental Conditions | Exposure Time in min. with end. temp. | Metal Instruments in Liquid | Growth in *B. subtilis* strips | Growth in control test tubes | Vapor at the end of process |
|---|---|---|---|---|---|
| Microwave heat & chemical disinfectant | 3 min, 65° C. | yes | none | yes | no |
| Microwave heat (no chemical) | 3 min, 56° C. | no | yes | yes | no |
| Chemical disinfectant (no microwave heat) | 3 min., 56° C. | no | yes | yes | no |
| Chemical disinfectant (no heat whatsoever) | 3 min, 25° C. | yes | yes | yes | no |
| Microwave heat & chemical disinfectant | 4 min, 83° C. | yes | none | yes | yes |

From Table 2, it is apparent that microwave heat alone without the chemical disinfectant (replaced by tap water) cannot kill all *B. subtilis* on the strips. The chemical disinfectant alone (no microwave heat) at 56° C. exhibited growth in some *B. subtilis* strips. The chemical disinfectant alone at room temperature did not kill *B. subtilis* on any strip.

Thus, the data of Table 2 demonstrates that the biocidal composition of the invention coupled with microwave irradiation at an energy density level higher than 0.018 Watt/$cm^3$ exhibited a biocidal synergistic effect. Table 2 data also shows that to avoid the emission of noxious vapor at the end of a decontamination batch, the end temperature should not be higher than 65° C.

Example 3

Potential corrosion on metals other than stainless steel was investigated under the 3 min/65° C. experimental conditions. The dental tools were replaced by a dozen hollow anodized aluminum tubes (length 25 cm, int. diam. 2–5 mm). No apparent damaged was observed after several days of repeated exposures.

Example 4

In the original text of Content and Format of Premarket Notification (510 k) Submissions for Liquid Chemical Germicides (Jan. 1982), several definitions are given by the regulatory agencies of a High level disinfectant. On page 5, for instance, the following definition is provided:

A GERMICIDE THAT KILLS ALL MICROBIAL PATHOGENS EXCEPT LARGE NUMBERS OF BACTERIAL ENDOSPORES, WHEN USED ACCORDING TO LABELING.

This definition was repeated in the April 26, 1995 revised edition printed by the FDA on pages 5 and 36. High level Disinfection claims require a showing that the contact time for high level disinfection is sufficient to achieve a 6 log reduction of *Mycobacterium tuberculosis* var. *bovis* under the worst case conditions of germicide compositions. Testing may be conducted with Mycobacterium in suspension or on carriers, but the number of organisms on the carriers must be quantitated.

Tuberculocidal and virucidal efficacy was determined using different chemical formulations set forth in Tables 3 and 4 respectively:

TABLE 3

TUBERCULOCIDAL ACTIVITY WITH 3 DIFFERENT SAMPLES

| Condition in Reaction Vessel | Exposure Time | End-Temperature with Microwave | Percent Reduction of *M. bovis* var. BCG** |
|---|---|---|---|
| 1.0 ml *M. bovis* plus 49.0 ml of Sample A. ($H_2O_2$ plus 5% acetic acid) | 0.5 min 1.0 1.5 2.0 3.0 | 30° C. 35° 43 45 56 | 99.86% 99.90 99.980 99.985 >99.9999% (no surviving colonies) |
| 1.0 ml *M. bovis* plus 49.0 ml of Sample B $H_2O_2$ plus 5% citric acid | 0.5 min 1.0 2.0 3.0 | 31° C. 35 45 60 | 99.865% 99.90 99.998 >99.9999% (no surviving colonies) |
| 1.0 ml *M. bovis* plus 49.0 ml of Sample C ($H_2O_2$ plus 5% lactic acid) | 0.5 1 2 3 | 31° C. 35 45 66 | 99.86 99.90 99.998 >99.999% (no surviving colonies) |

**Weight percent reduction of *M. bovis* var. BCG is given by the formula: $[1.0 - S^+/S_0] \times 100$
wherein $S_0$ is the original number of *M. bovis* var. BCG in the vessel at zero time. In this experiment, it was equal to $5.2 \times 10^6$ CFU.
$S^+$ is the number of surviving colonies of *M. bovis* var. BCG at various exposure times.

TABLE 4

VIRUS INACTIVATION OF SAMPLE B AFTER ONE DAY REUSE AT 60° C. WITH 3 MIN EXPOSURE TIME

|  | Titer untreated virus | Titer if virus exposed to microwave & chemical | Inactivation |
|---|---|---|---|
| Polio virus type 2 | $10^6$ | $10^0$ | 6 logs |
| Herpes simplex-type 1 | $10^{5.5}$ | $10^0$ | 5.5 logs |
| Influenza A virus (PR8) | $10^{5.5}$ | $10^0$ | 5.5 logs |

As set forth in Table 3, the biocidal compositions were always a mixture of 10 weight percent of concentrated hydrogen peroxide diluted down to about 6 to about 7.5 weight percent with a weak organic acid, such as acetic acid, $C_2H_4O_2$, citric acid, $C_6H_8O_7$ or lactic acid, $C_3H_6O_3$.

The quantitative tuberculocidal efficacy test employed is an EPA approved method based on the modified work of Ascenzi et al (Appl. Environ. Microbiol, 93: 2189–2192, 1987). In the test, 1.0 ml of *M. bovis* var. BCG was added to 49.0 ml of the tested disinfectants in a 750 ml. reaction vessel previously described (Rubbermaid, microwave container). The reaction vessel holds more that 10 Colony Forming units (CFU) of *M. bovis.* var BCG. The reaction vessel with its content was microwave irradiated during 3 minutes and reached an end-temperature of 65° C. At various exposure time intervals such as 0.5, 1.0, 1.5, 2.0, 3.0 and 5 min., 1.0 ml is removed from the reaction vessel added to neutralizing medium (phosphate buffered saline plus catalase), and immediately further diluted and measured for surviving CFU of *M. bovis.* var. BCG. This mycobacterium was very slow to grow and colonies were counted only after 28 days incubation period at 37 degrees C. The weight percent reduction of *M. bovis* var BCG are given in table 3 for various compositions and exposure times. *M. tuberculosis* var *bovis* is more difficult to kill than most other non-sporulated bacteria (such as *P. aeruginosa, S. aureus* and *S. cholerasuis*) whose kill is required to make a hospital germicide disinfectant claim. Likewise, *Trichophyton mentagrophyte* (ATCC 9533) is the requisite fungus for making an EPA claim according to the official method of the Association of Official Analytical Chemists. Dilution tests according to the AOAC procedure were conducted in the presence of 3 weight percent serum. All tests with the above referenced bacteria showed complete kill in 3 minutes at 60° C. in the presence of microwave irradiation (energy density: 0.018 watt/cm$^3$). The biocidal composition used for these experiments contained a 6 to 7.5 weight percent dilution of hydrogen peroxide mixed with a vinegar of 5 weight percent acidity.

Example 5

Virucidal capabilities of the process of the invention was further demonstrated by testing with one hydrophilic polio virus type 2 and two lipophilic viruses (herpes simplex type 1) and influenza A virus, (PR8). The viruses were dried on stainless steel penicylinders according to the AOAC method (paragraph 4.007 through 4.014) and treated for 3 minutes with microwave irradiation (60° C. and the chemicals (hydrogen peroxide diluted with a 5 weight percent citric acid solution). The results given at the bottom of Table 4 show complete eradication of the viruses by a sample which had already been used five times in succession in one day. This indirectly confirmed that the biocidal Sample B contained still enough active ingredient at the end of one day reuse.

In accordance with the above it must be well understood that according to the desired results the present invention can be applied with different sizes and shapes of containers with different microwave power units and with different exposure times as long as one can achieve a full destruction of microbial spores, microorganisms and viruses present on the surface of the instruments. Still without departing from the scope of the invention the structural details of the described apparatuses (shape of containers to accommodate various instruments, microwave cavity sizes and corresponding supporting shelves etc) may be modified and that certain members may be replaced by other equivalent means (Magnetrons replaced by Klystrons or Amplitron tubes). The present invention can be used to sterilize or disinfect any solid interface accessible to the liquid biocidal agent. Microwave radiation will not only penetrate the different materials supporting the microorganisms but will also act upon the molecular structure of the microorganisms themselves. In other words many intricate contaminated surfaces such as channels of fiber optic devices, small tubings in both rigid and flexible endoscopes, laparoscopes etc. could be decontaminated as well as simpler instruments such as front surface dental mirrors, explorers, scalpels, scissors etc.

The invention may take form in various steps and arrangements of steps and in various parts and arrangements of parts. Various modifications may be made therefore in the nature, composition, operation and arrangement of the various elements, steps and procedures described herein without departing from the spirit and scope of the invention as defined in the following claims.

I claim:

1. A method for disinfecting or sterilizing a surface of a dental, medical or laboratory instrument which comprises exposing the instrument to a biocidal solution consisting essentially of hydrogen peroxide and a weak organic acid selected from acetic acid, citric acid, lactic acid and white distilled vinegar or a mixture thereof while simultaneously subjecting the instrument to microwave irradiation, the temperature of the biocidal solution being less than or equal to 65° C.

2. The method of claim 1, wherein the instrument to be disinfected or sterilized is placed into a vessel composed of a material which is at least partially transparent to microwave energy and further wherein the vessel contains the biocidal solution.

3. The method of claim 2, further comprising removing the vessel from the biocidal solution and microwave irradiation upon the sound of an automatic acoustic signal.

4. The method of claim 2, wherein the minimum average of radiated energy level inside the vessel is approximately 0.01 watt/cm$^3$.

5. The method of claim 1, wherein the amount of weak organic acid in the biocidal composition is an amount sufficient to render about 6 to about 7.5 weight percent of hydrogen peroxide.

6. The method of claim 1, wherein the biocidal solution contains approximately 10 weight percent hydrogen peroxide.

7. The method of claim 1, wherein the applied microwave energy is within the frequency range from about 100 to about 23,000 MHZ.

8. The method of claim 7, wherein the applied microwave energy frequency is approximately 2450 MHZ (±25 MHZ).

9. The method of claim 1, wherein the microwave irradiation is a continuous or pulsed wave emission having a repetition rate of the order of between about one per nanosecond and about one per minute.

10. The method of claim 1, wherein the weak organic acid has a pKa greater than or equal to 4.0.

11. The method of claim 1, wherein the biocidal solution further contains a stabilizer.

12. The method of claim 1, wherein the biocidal agent further contains an anticorrosion agent.

13. The method of claim 1, wherein the biocidal agent further contains a buffering agent.

14. The method of claim 1, wherein the pH of the biocidal solution is between about 1 to about 7.

15. The method claim 1, wherein the instrument is an endoscope.

16. The method of claim 1, wherein the instrument is one used in veterinary medicine.

17. The method of claim 1, wherein the instrument is one used in medical testing, diagnosis or evaluation.

18. The method of claim 1, wherein the instrument is a dental instrument.

19. The method of claim 17, wherein the instrument is one used in a hospital.

20. The method of claim 17, wherein the instrument is one used in a doctor's office.

21. The method of claim 1, wherein the instrument is one used in a coroner's office or laboratory.

22. The method of claim 1, wherein the biocidal solution contains from about 0.1 to about 5 weight percent of a hydrogen peroxide compatible surfactant.

23. A method for disinfecting or sterilizing a surface of a dental, medical or laboratory instrument which comprises exposing the instrument to a biocidal solution consisting essentially of hydrogen peroxide and a weak organic acid selected from acetic acid, citric acid and lactic acid or white distilled vinegar or a mixture thereof while simultaneously subjecting the instrument to microwave irradiation at the frequency range from about 100 to about 23,000 MHZ.

24. The method of claim 23, wherein the biocidal solution contains approximately 10 weight percent hydrogen peroxide.

25. The method of claim 23, wherein the concentration of hydrogen peroxide is between about 6 and about 7.5 percent.

26. The method of claim 23, wherein the instrument to be disinfected or sterilized is placed into a vessel composed of a material which at least partially transparent to microwave energy and further wherein the vessel contains the biocidal solution.

27. The method of claim 23, wherein the applied microwave energy frequency is approximately 2450 MHZ (±25 MHZ).

28. The method of claim 23, wherein the instrument is one used in a coroner's office or laboratory.

29. The method of claim 23, wherein the instrument is a dental instrument.

30. The method claim 23, wherein the instrument is an endoscope.

31. The method of claim 23, wherein the instrument is one used in veterinary medicine.

32. The method of claim 23, wherein the instrument is one used in medical testing, diagnosis or evaluation.

33. The method of claim 23, wherein the instrument is one used in a hospital.

* * * * *